United States Patent [19]

Streicher et al.

[11] Patent Number: 5,609,734
[45] Date of Patent: Mar. 11, 1997

[54] COMBINED DISTILLATION AND PERMEATION PROCESS FOR THE SEPARATION OF OXYGENATED COMPOUNDS FROM HYDROCARBONS AND USE THEREOF IN ETHERIFICATION

[75] Inventors: Christian Streicher, Rueil Malmaison; Lionel Asselineau, Paris, both of France

[73] Assignee: Institut Francais du Petrole, Rueil-Malmaison, France

[21] Appl. No.: 336,222

[22] Filed: Nov. 7, 1994

[30] Foreign Application Priority Data

Nov. 5, 1993 [FR] France .................................. 93 13319

[51] Int. Cl.⁶ ...................................................... B01D 3/36
[52] U.S. Cl. ........................... 203/39; 203/98; 210/634; 210/649
[58] Field of Search ........................... 203/28, 29, 39, 203/86, 94, 98, 99; 568/697, 698, 699; 585/818, 802; 210/634, 640, 649

[56] References Cited

U.S. PATENT DOCUMENTS

| | | | |
|---|---|---|---|
| 4,740,632 | 4/1988 | Anderson et al. | 568/697 |
| 4,759,850 | 7/1988 | Farnand et al. | 210/654 |
| 4,774,365 | 9/1988 | Chen et al. | 568/697 |
| 5,152,898 | 10/1992 | Bartels | 203/86 |
| 5,292,963 | 3/1994 | Kanji et al. | 568/697 |

FOREIGN PATENT DOCUMENTS 0459627  12/1991  European Pat. Off. .

*Primary Examiner*—Timothy McMahon
*Attorney, Agent, or Firm*—Millen, White, Zelano, & Branigan, P.C.

[57] ABSTRACT

A process for the separation of oxygenated compounds, containing mainly methanol and possibly a minor amount of water and/or dimethyl ether, from a mixture of hydrocarbons containing 3 to 8 carbon atoms containing said oxygenated compounds. The mixture is distilled in a distillation zone (D). A gaseous distillate (line 2) is taken overhead which contains methanol, possibly water, possibly dimethyl ether, and hydrocarbons. The gaseous distillate is separated in a separator (B) and at least one organic liquid phase is recovered (line 6) and sent as a reflux to the head of distillation zone D. An aqueous liquid phase (line 5) may possibly be recovered, also a gaseous phase (line 4). A phase (line 8) is extracted as a side stream from the distillation zone and sent to a permeation zone (PV) comprising at least one membrane which is selectively permeable to methanol; a permeation step is carried out on said phase. At least one methanol-enriched permeate (line 14) is recovered downstream of the permeation zone, preferably as a vapor, and at least one residue (line 11) is recovered upstream which is optionally recycled to the distillation zone. The purified hydrocarbon mixture is extracted (line 16) from the bottom of the distillation column.

21 Claims, 1 Drawing Sheet

COMBINED DISTILLATION AND PERMEATION PROCESS FOR THE SEPARATION OF OXYGENATED COMPOUNDS FROM HYDROCARBONS AND USE THEREOF IN ETHERIFICATION

BACKGROUND OF THE INVENTION

The invention concerns a process for the separation of oxygenated compounds (methanol, dimethyl ether, water) from a mixture of hydrocarbons containing 3 to 8 carbon atoms, and the use thereof.

Alkyl tertioalkyl ethers are used as high octane number additives for lead-free or reduced lead petrols (i.e., fuels).

The most frequently used alkyl; and tertioalkyl ethers are produced by addition of methanol to a tertiary olefin.

Methyl tertiobutyl ether (MTBE), for example, is obtained by the addition of a molecule of methanol to a molecule of isobutene.

Similarly, tertioamylmethyl ether (TAME) is obtained by the addition of a molecule of methanol to a molecule of isoamylene.

These ethers are normally synthesized in a process generally involving introducing a liquid phase comprising a certain quantity of methanol and the tertiary olefin(s) required for the reaction into one or more reactor(s) containing a suitable catalyst. A high conversion factor for the tertiary olefins requires an excess of alcohol to be introduced which must then be separated from the effluent from the reaction zone for recycling. The tertiary olefins are generally present in a hydrocarbon mixture. Isobutene used for MTBE synthesis, for example, is most often contained in a C4 steam cracking or catalytic cracking cut. The hydrocarbons which are thus introduced into the reaction zone with the tertiary olefin(s) do not usually react, or react only slightly, and are thus also found in the effluent from the reaction zone.

The effluent from the reaction zone is thus a mixture containing the ether produced by the reaction, excess unreacted alcohol, unreacted hydrocarbons and small quantities of products produced in secondary reactions such as methanol etherification which produces a molecule of water and a molecule of dimethyl ether from two molecules of methanol.

A variety of processes for the separation of this mixture have been proposed. The most frequently employed process consists in sending the effluent from the reaction zone to a distillation column to produce an effluent containing all the ether at the bottom along with, possibly, a portion of the alcohol present in the effluent from the reaction zone. A raffinate constituted by the hydrocarbons and a portion, preferably all, of the alcohol present in the effluent from the reaction zone, is taken overhead. The alcohol content in the raffinate is generally 0.1% to 10% by weight, preferably 1% to 5% by weight. The alcohol must then be separated from the raffinate for recycling to the reaction zone. The raffinate also contains water and dimethyl ether, produced in secondary reactions, as impurities. Even though these oxygenated products are present in small quantities (generally 0.01% to 0.1% by weight), in general they too must be eliminated from the raffinate. Once purified, the raffinate is usually used as a feedstock for other reactions (for example, alkylation); because of the catalysts used in these subsequent reactions, severe restrictions are usually imposed on the total amount of oxygenated compounds (1 to 50 ppm depending on the case).

In certain processes, the effluent from the reaction zone is sent to a catalytic distillation column, either to increase the tertiary olefin(s) conversion rate or to reduce the excess of alcohol used. Whatever the case, the raffinates taken overhead from the catalytic distillation columns have analogous compositions to those of raffinates taken overhead from conventional distillation columns, but with slightly lower alcohol contents.

The methanol contained in the raffinate cannot be eliminated by simple distillation because of azeotrope formation between the methanol and the hydrocarbons. It can, however, be removed by various methods. The most popular process used is described in U.S. Pat. No. 3,726,942 and involves washing the raffinate with water. This process is efficient but requires distillation of the water/alcohol mixture thus produced in order to recycle the alcohol to the reaction zone. This distillation step makes the water washing process fairly expensive as regards investment and energy consumption.

A further water washing process is described in European patent EP-A-459,627.

Other variations of this water washing process have been described. U.S. Pat. No. 4,118,425, for example, describes a process in which the effluent from the reaction zone itself is washed with water before entering the distillation column, a raffinate which is free of alcohol being taken overhead. Here too, the water/alcohol mixture produced during the washing step must be distilled to recycle the alcohol to the reaction zone.

The water washing process has the further disadvantage of not being able to eliminate oxygenated impurities such as dimethyl ether from the raffinate, whichever variation is used. Still further, the water washed raffinate is, of course, saturated with water.

U.S. Pat. No. 4,740,631 describes a process in which the methanol is eliminated from the raffinate by adsorption on an appropriate molecular sieve (zeolites) with subsequent regeneration of the molecular sieve by the hydrocarbon mixture constituting the feedstock for the reaction zone. This process has the advantage of removing the distillation step required by water washing processes. Unfortunately, as with all adsorption processes, this is a discontinuous process since the molecular sieve used has to be regenerated periodically. This means that at least two adsorption beds and a relatively complex operating procedure must be used to carry out the alternating cycles of adsorption and regeneration. In addition, as with water washing processes the adsorption process cannot eliminate the dimethyl ether present in the raffinate. Here again, subsequent purification steps are necessary, for example by adsorption on other molecular sieves or by distillation, in order to achieve the low total oxygenated compound contents generally required.

A simpler methanol elimination process is described in U.S. Pat. No. 4,740,632. In this process, the raffinate is constituted by a mixture of methanol and hydrocarbons containing 4 carbon atoms. Since the hydrocarbons are then sent to an alkylation unit which is catalysed by sulphuric acid, the spent sulphuric acid from the alkylation unit is used to treat the raffinate. This produces an organic phase containing methanol-free hydrocarbons which is sent to the alkylation unit and an aqueous phase containing the methanol which has reacted with the sulphuric acid. This aqueous phase is then sent to a regeneration unit to recover the acid. While this process is very simple, it is quite expensive when the raffinate to be treated contains more than 0.5% by weight of methanol, which is often the case, since the methanol which has reacted with the acid cannot be recovered during the acid regeneration step for recycling to the reaction zone.

Another method of separating the alcohol in the raffinate is to bring the mixture for separation into contact with a membrane which is selectively permeable either to the alcohol, which is the most frequent and most advantageous case bearing in mind the small amounts of alcohol to be extracted, or to the hydrocarbons.

U.S. Pat. No. 4,759,850 describes a method of separating methanol from a mixture of hydrocarbons and/or ethers by reverse osmosis.

Better selectivities, and thus purer products, have however been obtained by pervaporation. In this process, the mixture for separation is brought into contact, as a liquid and at an appropriate temperature and pressure, with one face of a membrane. A vacuum is applied to the other face. The membrane is selective to one of the constituents of the mixture which preferentially diffuses through the membrane. A permeate is recovered downstream of the membrane (vacuum side) which is enriched in this constituent and which can then be compressed or condensed at low temperature. From the upstream side of the membrane, a residue is obtained containing of the initial mixture depleted in the constituent. Because of its selectivity, this process is of particular advantage when azeotropic mixtures are to be separated.

Most of the pervaporation membranes in current use are selective to water in mixtures of organic products. There are some, however, which are selectively permeable to alcohols in organic mixtures.

U.S. Pat. Nos. 4,798,674, 4,877,529, 4,960,519, 5,152,898, German patent DE-A-4,234,521 and European patent application EP-A-92117467.8 describe various such membranes and their use in extracting alcohols with less than three carbon atoms, preferably methanol, by pervaporation from mixtures containing other oxygenated organic compounds such as ethers, esters, aldehydes or ketones.

U.S. Pat. No. 4,774,365 describes a process for the separation of alcohol present in the effluent from the reaction zone in an etherification process using a pervaporation membrane.

In a first embodiment of the process, the effluent from the reaction zone passes over a pervaporation membrane which selectively extracts alcohol. The extracted alcohol is recycled to the reaction zone. The alcohol-depleted residue obtained is then distilled. In this embodiment, an alcohol-free ether can be obtained from the bottom of the distillation column. However, in order for the raffinate taken overhead from this distillation column to be completely free of alcohol, all the alcohol present in the effluent from the reaction zone must have been eliminated by the pervaporation unit. It is, however, known that pervaporation, in common with all processes using membranes, becomes very expensive when the last traces of a product have to be removed (in general, dropping to concentrations of less than 0.1% is not economical). Thus it is difficult to use this embodiment to produce a raffinate with a very low alcohol content.

The same document describes another embodiment in which the effluent from the reaction zone is sent directly to the distillation column. A liquid fraction is removed as a side stream from the column and sent to a pervaporation membrane which extracts a portion of the alcohol present in this liquid fraction. The extracted alcohol is recycled to the reaction zone while the alcohol-depleted residue is returned to the distillation column. Again, this embodiment produces an alcohol-free ether at the bottom of the distillation column. However, because alcohol is entrained in the hydrocarbons by azeotropy, it is still difficult for a raffinate (the value given in Example 2 of the patent document) containing less than 0.1% by weight of residual alcohol to be taken overhead from the distillation column. This remains true for all combinations of the two embodiments, as shown in Example 2 of the document.

Further, apart from using a membrane which will simultaneously extract methanol and dimethyl ether from a mixture containing hydrocarbons and/or other ethers, it appears clear that, whatever the embodiment used, this process cannot eliminate or reduce the amount of dimethyl ether present in the effluent from the reaction zone which then appears in the raffinate.

SUMMARY OF THE INVENTION

The present invention therefore aims to provide a process for the separation of methanol from a mixture of hydrocarbons containing 3 to 8 carbon atoms, combining a distillation step with a pervaporation step in order to obtain a major portion of these hydrocarbons (more than 95%, preferably more than 99%) with a very low residual concentration of methanol, for example less than 50 ppm by weight.

The process of the present invention also eliminates dimethyl ether and/or water when present in the mixture of hydrocarbons and methanol, to produce said major portion of hydrocarbons with a very low total oxygenated compound content, for example less than 50 ppm by weight.

The present invention also provides a process for the synthesis of ethers from methanol and a mixture of hydrocarbons containing 3 to 8 carbon atoms (C3, C4, C5, C6, C7 or C8 cuts and/or mixtures thereof) using the separation process of the invention in which the methanol produced by the separation process is recycled to the reaction zone.

The process of the present invention is particularly suitable for mixtures of hydrocarbons (C3 to C8 cuts and/or mixtures thereof) obtained, following separation of the ether produced, in etherification processes using methanol, by distillation and/or catalytic distillation of the effluent from the reaction zone. These mixtures generally contain 0.1% to 20% by weight of methanol, preferably 0.5% to 5% by weight of methanol. They also generally contain 10 ppm by weight to 1% by weight of water, preferably 100 to 1000 ppm by weight of water, as well as 10 ppm by weight to 1% by weight of dimethyl ether, preferably 100 to 1000 ppm by weight of dimethyl ether.

More precisely, the invention concerns a process for the separation of oxygenated compounds, containing mainly methanol and possibly a small amount of water and/or dimethyl ether, from a mixture of hydrocarbons containing 3 to 8 carbon atoms containing the oxygenated compounds, characterised in that the mixture is distilled in a distillation zone under appropriate pressure and temperature conditions.

A gaseous distillate is taken overhead which contains methanol, water, dimethyl ether and the hydrocarbons. The distillate is condensed and at least partially recycled.

A gaseous, liquid or mixed phase is extracted as a side stream from the distillation zone and sent under suitable conditions to a permeation zone comprising at least one membrane which is selectively permeable to methanol; a permeation step is carried out on said phase.

At least one methanol-enriched permeate is recovered downstream of the permeation zone, preferably as a vapor, and at least one residue is recovered upstream of the permeation zone. The purified hydrocarbon mixture is extracted from the bottom of the distillation zone.

The term "permeation zone" means a pervaporation zone where a liquid phase is brought into contact with the upstream face of the membrane, or a vapor permeation zone when using a gaseous or mixed phase.

In accordance with one feature of the process, the side stream phase is extracted from at least one tray in the distillation zone, where the methanol concentration is at least equal to that of the methanol in the hydrocarbon mixture supplied to the distillation zone, preferably from the tray where the methanol concentration is substantially maximal.

The extracted organic phase contains methanol and hydrocarbons and may also contain a minor amount of water and dimethyl ether. Under these conditions, if the selected membrane is impermeable to dimethyl ether, the latter is recovered in the residue and recycled. On the other hand, if the selected membrane is permeable to dimethyl ether, the latter is found at least in part in the permeate.

In accordance with a further feature of the process, the pressure in the permeation zone (on the upstream face of the membrane) may be greater than, equal to or less than the pressure in the distillation zone.

When the liquid phase is taken as a side stream, the temperature and pressure conditions can be adjusted to allow said phase to be admitted into the pervaporation zone using appropriate equipment: heat exchangers, pumps, or pressure reducing valves.

If a gaseous or mixed phase is extracted, it is preferably admitted directly to the vapor permeation zone. Here too, the temperature and pressure conditions can be adjusted to preferred values for admission into the vapor permeation zone using appropriate equipment: heat exchangers, pumps, compressors or pressure reducing valves.

In a still further feature of the process, the residue which has not passed through the membrane is recycled to the distillation zone. The residue can be a liquid, vapor or mixed phase. In order to recycle it to the distillation zone, it must be at a pressure at least greater than that in the distillation zone. If this is not the case, it can be brought to the correct pressure using appropriate equipment: pumps, compressors. In certain cases, it is of advantage to modify the temperature of the residue before its admission into the distillation zone by increasing or decreasing the temperature by passage through one or more heat exchanger(s) before or after passing through the pressure increasing equipment, if required.

Advantageously, the residue is recycled to the distillation zone to a lower tray than that from which the side stream is extracted. Preferably, the residue is recycled to the tray with substantially the same composition as the residue.

In a further feature of the process, at least a portion of the gaseous distillate is condensed and recovered at least a portion of an organic liquid phase is recovered to act as a reflux. An aqueous phase may be recovered, also a gaseous or liquid phase containing methanol and dimethyl ether.

DETAILED DESCRIPTION OF THE DRAWINGS

Figure 1:
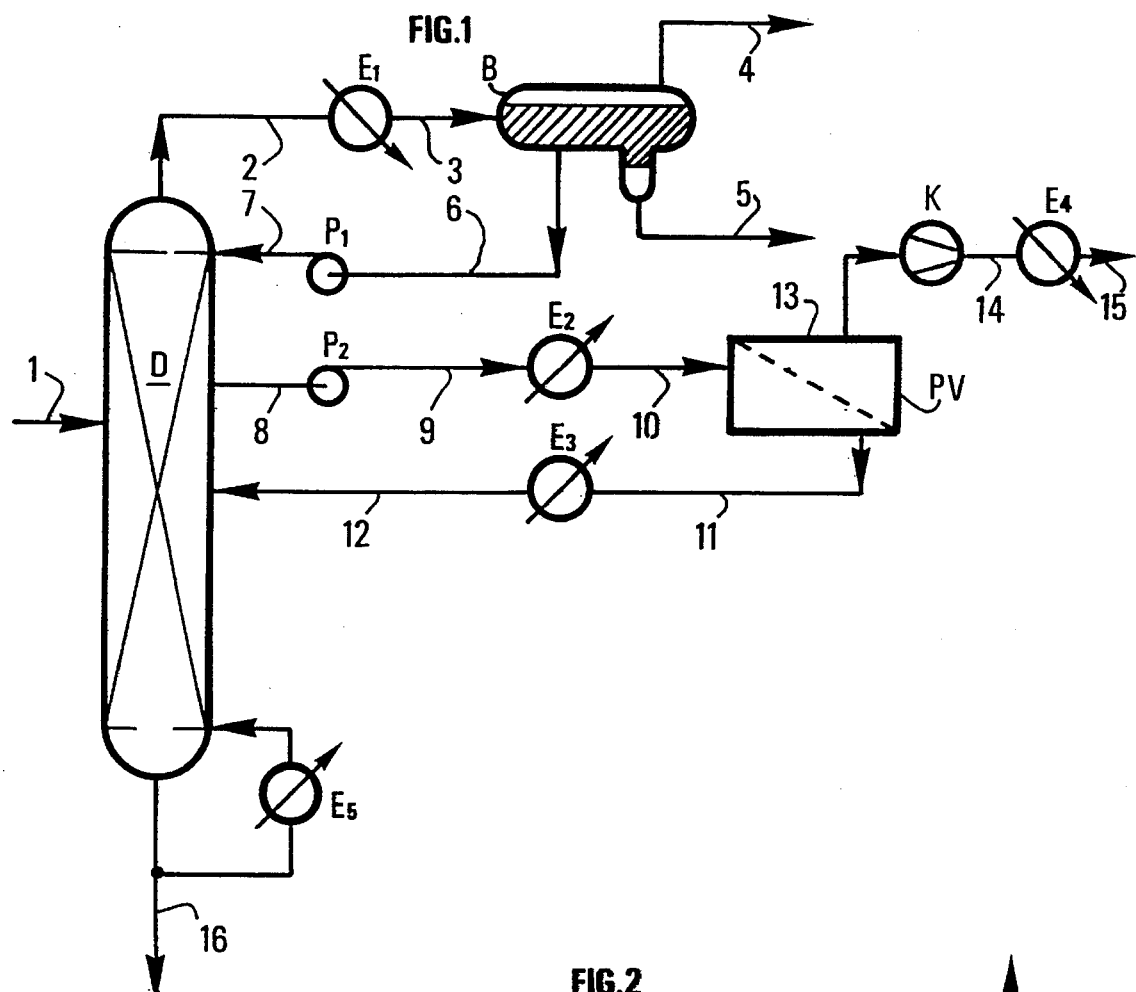
FIG. 1 represents a distillation/preparation apparatus in accordance with the invention. A feed containing hydrocarbons and oxygenated hydrocarbons is subjected to distillation, and a side-stream of high alcohol content is removed and subjected to a selectively permeable membrane. A residue is returned to distillation.

An advantageous embodiment will now be described with reference to FIG. 1.

The mixture for separation, containing for example up to 5% by weight of methanol (this amount depends on the hydrocarbon cut introduced into the etherification reactor) is sent via line 1 to distillation column D. This column generally operates at a pressure of more than 1 bar, advantageously between 2 and 35 bar. It is heated by reboiler E5. The bottom temperature is generally between 70° C. and 200° C. The top temperature is generally between 40° C. and 120° C. The mixture for separation is preferably introduced into column D at the bubble point at the pressure used, to the tray with the closest composition to that of said mixture, for example to the upper part of the column in the case of mixtures containing 1% to 5% by weight of methanol.

A gaseous distillate is taken overhead via line 2 from the column, constituted by 0.1% to 5% by weight of water when present in the mixture for separation, 0.5% to 10% by weight, ie., the majority of any dimethyl ether which may be present in the mixture for separation, 0.5% to 10% by weight of methanol, and the remainder constituted by hydrocarbons. This vapor is then partially condensed in exchanger E1 then sent via line 3 to separator B. Following decantation in separator B, a residual vapor containing 0.5% to 10% by weight of methanol, 0.1% to 5% of water if present in the mixture for separation, 0.5% to 20% by weight of dimethyl ether if present in the mixture for separation, and hydrocarbons, leaves via line 4. The hydrocarbons lost in this residual vapor represent less than 5%, preferably less than 1% of the hydrocarbons present in the mixture for separation. The residual vapor can then be readily used as a fuel, and this allowable loss of hydrocarbons does not affect process profitability.

When the mixture for separation contains water, the major portion thereof is recovered from separator B via line 5 in the form of an aqueous liquid normally containing 1% to 70% by weight of methanol and 0.1% to 5% by weight of hydrocarbons and/or dimethyl ether if present in the mixture for separation.

The quantity of aqueous liquid phase obtained depends on the amount of water in the mixture for separation. In mixtures which are normally used in etherification processes, which contain less than 0.1% of water, this aqueous liquid phase normally represents less than 0.1% by weight of the quantity of mixture treated by the process. It can then either be sent to a conventional waste water treatment unit when it contains low amounts of methanol, or be eliminated by combustion if, for example it contains more than 50% by weight of methanol, the loss of methanol. Here too, the methanol thus lost and the cost of the treatment for this aqueous phase does not affect process profitability.

Finally, the major portion of the liquid phase obtained from separator B is an organic liquid phase with a composition close to that of the vapor taken overhead from distillation column D. This organic liquid phase is sent to pump P1 via line 6 then injected as a reflux to the top of column D via line 7. The amount of reflux used normally represents 0.3 to 3 times, preferably 0.5 to 1.5 times the mass flow rate of the mixture for separation constituting the feed to distillation column D.

A liquid fraction is extracted as a side stream from distillation column D via line 8. This side stream is preferably taken from the tray where the methanol concentration in the liquid phase is maximal. The liquid fraction removed generally has a methanol concentration greater than that of the mixture for separation which constitutes the feed to the distillation column. The mass flow rate of the removed liquid fraction can be greater than, equal to or less than that of the feedstock supplying the distillation column and depends on the methanol concentration in said liquid fraction and in the residue from pervaporation unit PV.

Pump P2 then brings the liquid fraction to the pressure required for transport to pervaporation unit PV and recycling to distillation column D. The liquid fraction is then delivered via line 9 to exchanger E2 where it is brought to a temperature appropriate for treatment by the pervaporation unit. This temperature depends in particular on the membrane used in the pervaporation unit. It is generally between 50° C. and 200° C., advantageously between 80° C. and 120° C.

The liquid fraction arrives in pervaporation unit PV via line 10.

Pervaporation unit PV consists of an assembly of one or more modules disposed in series and/or in parallel, inside each of which is a membrane which is selectively permeable to methanol, for example one of those described in U.S. Pat. Nos. 4,798,674, 4,877,529, 4,960,519, 5,152,898, German patent DE-A-4,234,521 and European patent application EP-A-92117467.8. The membrane separates each module into one or more upstream compartment(s) inside which the liquid fraction circulates and one or more downstream compartment(s) inside which the products which have passed through said membrane circulate, this vapor phase being termed the permeate. The downstream compartment(s) of the different module(s) is (are) at (a) pressure(s) below that of the liquid circulating upstream of the membrane. This (these) pressure(s) is (are) generally below 1 bar absolute (1 bar=$10^5$ Pa).

The pervaporation unit generally includes intermediate reheaters (not shown in FIG. 1) between two modules in series which compensate for cooling of the liquid circulating upstream of the membrane caused by evaporation of a portion of the constituents of said liquid.

Following any necessary compression using compressor K, the permeates recovered from each module are condensed in exchanger E4. While FIG. 1 only shows one compressor K and one exchanger E4, clearly when the pervaporation unit comprises several modules producing vapor phase permeates at different pressures, a plurality of compressors and/or exchangers may be used in series and/or in parallel.

A liquid permeate is thus recovered via line 15, generally constituted by more than 50% by weight, preferably more than 90% by weight of methanol. The exact composition of the permeate depends on the selectivity and surface area of the membrane used in pervaporation unit PV as well as on the methanol concentration in the liquid supplying this unit via line 10. In general more than 95%, preferably more than 99% of the methanol present in the feed for distillation column D is found in this liquid permeate.

The methanol-depleted liquid which circulates upstream of the membrane, the residue, is recovered via line 11. Each exchanger E3 brings this liquid to a temperature suitable for its return to distillation column D, generally to the temperature of the tray at which said liquid is to be reinjected. This liquid is supplied to distillation column D by line 12, preferably to the tray with the closest composition to that of said liquid.

Finally, the distillation residue leaving the bottom of the column via line 16 is mainly constituted by purified hydrocarbons. The operating conditions regarding the various supply flow rates and column efficiency are general adjusted so that more than 95%, preferably more than 99% of the hydrocarbons present in the mixture for separation are obtained with a water content of less than 10% by weight, preferably less than 1 ppm by weight, with a methanol content of less than 50 ppm by weight, preferably less than 5 ppm by weight and with a dimethyl ether content of less than 100 ppm by weight, preferably less than 10 ppm by weight.

One of the advantages of the process described is its great simplicity since it uses a minimum number of units (one distillation column and one permeation unit) to separate methanol, water and dimethyl ether simultaneously from a mixture of hydrocarbons and produces said hydrocarbons with very low oxygenated compound content, meaning that subsequent purification steps for these hydrocarbons are no longer necessary.

A further advantage of the process lies in the fact that it can function with a membrane which is selectively permeable to methanol without the membrane necessarily being permeable to water and/or dimethyl ether. The process of the invention can, of course, function advantageously with a membrane which is selectively permeable to methanol and water and/or dimethyl ether. While substantially all membranes known to be selectively permeable to methanol are also permeable to water, none are currently known which are also permeable to dimethyl ether.

A final advantage of the process of the present invention lies in the fact that, despite the very low methanol content in the final product, the permeation unit operates in a much wider range of methanol concentrations, generally between 0.1% by weight, preferably 0.5% by weight, for the residue and 20% by weight for the supply to said unit. This not only means that much lower membrane surface areas can be used compared to other processes using permeation units for this type of separation, but also that the permeate can be recovered downstream of the membrane in the vapor phase at substantially higher pressures, thus considerably reducing the power required to compress the permeate.

The process of the invention is thus particularly economical as regards both investment and energy consumption.

Finally, treating a phase which has been extracted as a side stream from the distillation column in the permeation unit, rather than treating a phase which has been taken overhead, means that the treated phase can contain a larger methanol concentration and a lower water content than that obtained overhead from the distillation column. This means that a permeate which is richer in methanol and less rich in water, and thus of higher quality, can be recovered for recycling to the etherification zone.

Simultaneous separation of methanol, water and dimethyl ether from a hydrocarbon mixture as described can advantageously be integrated into a process for the synthesis of ethers from methanol and tertiary olefins present in a mixture of hydrocarbons containing 3 to 8 carbon atoms (C3 to C8 cuts and/or mixtures thereof).

Figure 2:
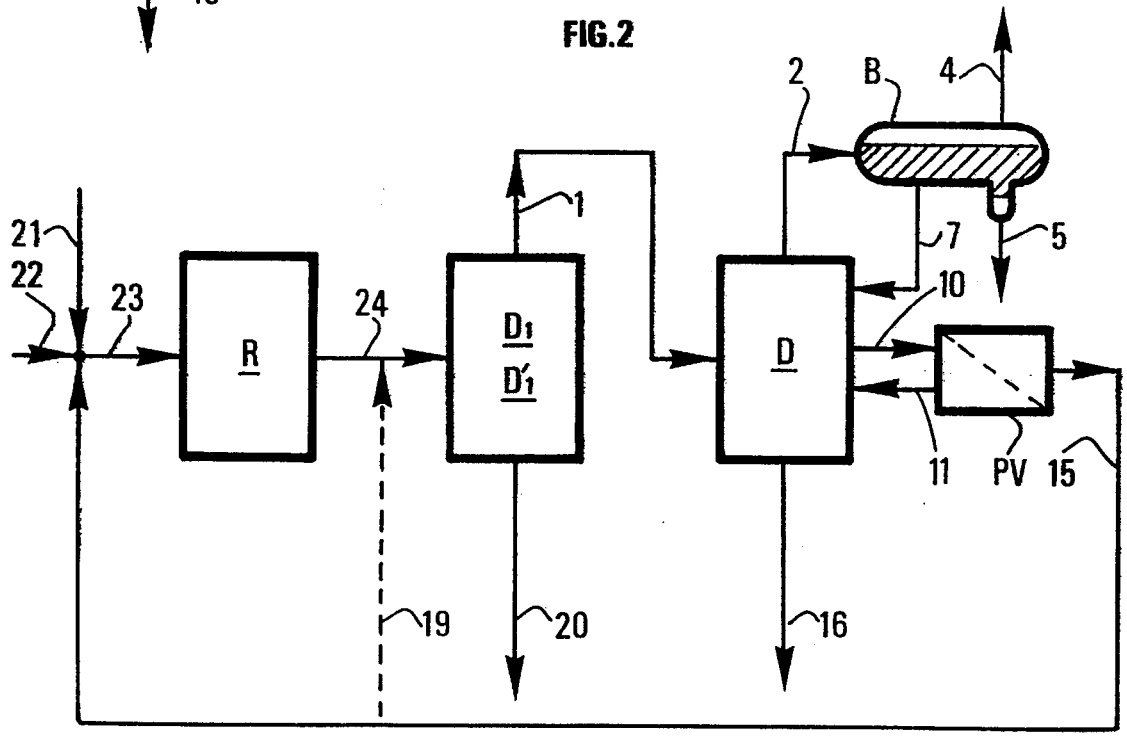
FIG. 2 represents an etherification process employing a pervaporation process in accordance with the invention in order to purify the products.

A process for the synthesis of ethers is described below with reference to FIG. 2.

The hydrocarbon mixture containing the tertiary olefins necessary for the reaction is supplied as a liquid via line 21. It is mixed with the methanol required for the reaction, supplied as a liquid via line 22 and a condensed and cooled permeate which is recycled from the pervaporation unit via line 15. The permeate is mainly constituted by the excess methanol used for the reaction along with a minor fraction, generally less than 0.5%, of unreacted hydrocarbons present in the effluent from the reaction zone.

The mixture obtained is introduced via line 23 into etherification reaction zone R where the tertiary olefins and methanol are converted into ethers. A secondary methanol etherification reaction produces small quantities of water and dimethyl ether in this reaction zone; these must then be at least partially eliminated.

The effluent from the reaction zone is then sent via line 24 to distillation column D1. An effluent mainly constituted by all the tertiary ethers produced (MTBE) is recovered from the bottom of the column. This effluent may also contain certain of the heaviest hydrocarbons present in the effluent from the reaction zone. This is particularly the case when the hydrocarbons constituting the feedstock for the reaction zone contain different numbers of carbon atoms (mixtures of C4 to C8 cuts). It should be noted that in this case, the hydrocarbons present at the bottom of distillation column D1 can generally be used as fuel constituents without the need for separation from the ethers produced. Finally, depending on the excess quantity of methanol used, a fraction of this methanol may also be present in the effluent from the bottom of distillation column D1. Since recovery of this methanol necessitates a supplementary fractionation step, it is generally preferable to limit the excess of methanol used to concentrations such that all the excess methanol is recovered in the effluent taken overhead from distillation column D1. The overhead effluent also includes the major portion of unreacted hydrocarbons. It further comprises all the water and dimethyl ether present in the effluent from the reaction zone.

Alternatively, distillation column D1 can be replaced by catalytic distillation column D'1, to increase the tertiary olefin conversion rate and/or reduce the excess of methanol employed. The effluents from column D'1, will have analogous compositions to those from column D1, with reduced concentrations of methanol.

The overhead effluent from distillation column D1 (or D'1) is then sent via line 1 to the apparatus for carrying out the process of the invention.

It is thus sent to distillation column D. This column produces methanol-, dimethyl ether- and water-free hydrocarbons from the bottom.

The overhead vapor is sent from column D to separator B after partial condensation. A residual vapor is recovered via line 4 from separator B, consisting mainly of dimethyl ether and a minor fraction of methanol, water and the lightest hydrocarbons. The residual vapor can, for example, be used as a fuel gas.

An aqueous liquid phase is also recovered from separator B, via line 5, consisting mainly of water and a minor fraction of methanol with traces of dimethyl ether and dissolved hydrocarbons. This aqueous liquid phase is normally burnt or sent to a waste water treatment unit because of its low flow rate. It could, however, be fractionated by distillation to produce water which can be discharged, and methanol which can be recycled to the reaction zone.

Finally, an organic liquid phase is sent from separator B via line 7 as a reflux to distillation column D. The phase is mainly constituted by hydrocarbons containing small amounts of methanol, dimethyl ether and dissolved water.

A liquid fraction is removed from distillation column D as a side stream via line 10 and sent to pervaporation unit PV provided with a membrane which is selectively permeable to methanol. This liquid fraction is preferably removed from the tray in distillation column D in which the methanol concentration is substantially maximal.

Pervaporation unit PV produces a methanol-depleted residue via line 11 which is recycled to a lower tray than that of the side stream from distillation column D.

Pervaporation unit PV also produces a permeate which is recycled at least in part via line 15 to reaction zone R. It may also be recycled at least in part via lines 15 and 19 to distillation zone D'1, if this zone is a catalytic distillation zone. As mentioned above, this permeate is mainly constituted by the excess methanol used in reaction zone R. Depending on the operating conditions and the characteristics of the membrane in pervaporation unit PV, it may also contain differing proportions of water, dimethyl ether and hydrocarbons. The amounts of these recycled products are, however, sufficiently low not to have a significant impact of the operation of reaction zone R.

The following examples are given by way of illustration.

EXAMPLES

Example 1

In this Example, the concentrations of oxygenated compounds in a C4 cut containing methanol, water and dimethyl ether (for compositions, see Tables 1a and 1b) were reduced to very low values (<1 ppm by weight of water, <1 ppm by weight of methanol, 10 ppm by weight of dimethyl ether) using the process of the present invention (Example 1a) and a conventional process constituted by a pervaporation step followed by a distillation step (Example 1b).

Example 1a, Process of the Invention (FIG. 1)

A stainless steel distillation column D with a diameter of 100 mm containing 56 perforated trays spaced by 5 cm was used, also a stainless steel pervaporation module provided with a membrane with a selective layer of poly-4-vinyl pyridine cross linked with 1,4-dibromobutane which had been prepared using the method described in Example XVI of U.S. Pat. No. 5,152,898. The module was constituted by a stack of 2 elements each with an effective permeation surface area of 0.1 m$^2$. The total permeation surface area was thus 0.2 m$^2$.

The mixture for separation, SUPPLY, was introduced as a liquid phase at a temperature of 78.0° C. into distillation column D via line 1, to tray number 12. Column D was operated at an absolute pressure of 22 bar, measured in separator B. The temperature of column D was between 115.5° C. at the bottom and 80.4° C. at the top.

The vapor taken overhead from column D via line 2 was partially condensed then decanted in separator B. The temperature in separator B was 69.9° C. Gaseous phase C3 was extracted from separator B via line 4 and aqueous liquid phase WATER was extracted via line 5. The organic liquid phase obtained from line 6 was returned as reflux to the head of column D. The reflux ratio (ratio of the mass flow rate of the reflux liquid to the head of column D to that of SUPPLY) was 0.69.

The majority of purified C4 cut, PURIFIED C4, was recovered from the bottom of column D as a liquid phase.

A liquid phase, EXTRACTION, was extracted from tray number 8 of column D, at a temperature of 100.2° C., cooled to a temperature of 50.0° C. and supplied to pervaporation unit PV via line 10. Unit PV produced a vapor phase permeate, PERMEATE, via line 13, which was collected after condensation, and a liquid residue, RESIDUE, which was returned to tray 18 of column D after reheating to 106.0° C.

The material balance (flow rates and compositions by weight of the SUPPLY, C3, WATER, PURIFIED C4, EXTRACTION, PERMEATE and RESIDUE streams) from this process are shown in Table 1a.

TABLE 1a

Material balance from process of the invention, Example 1a

| SUBSTANCE (WT %) | SUPPLY | C3 | WATER | PURIFIED C4 | EXTRACTION | PERMEATE | RESIDUE |
|---|---|---|---|---|---|---|---|
| C3 | 1.54 | 66.15 | 3.52 | 1.20 | 9.23 | 1.00 | 9.72 |
| C4 | 95.94 | 25.92 | 0.88 | 98.80 | 84.54 | 9.34 | 89.11 |
| Methanol | 2.44 | 2.64 | 48.73 | <1 ppm | 5.74 | 89.27 | 0.68 |
| Water | 0.05 | 0.53 | 45.16 | <1 ppm | 0.02 | 0.34 | <1 ppm |
| Dimethyl-ether | 0.03 | 4.76 | 1.72 | 10 ppm | 0.47 | 0.05 | 0.49 |
| Flow rate $(g \cdot h^{-1} \cdot m^{-2})$ | 4000.0 | 21.3 | 3.3 | 3868.4 | 1872.3 | 107.0 | 1765.3 |

Example 1b (Comparative)

This process consisted in the simple succession of a pervaporation step PV for extracting the major portion of the methanol from the mixture for separation, followed by a distillation step D to eliminate the residual oxygenated compounds (mainly traces of methanol and dimethyl ether, the water being substantially entirely extracted during the pervaporation step).

The same distillation column D was used as for Example 1a, operated at an identical pressure (22 bar in separator B). The pervaporation module PV used was provided with the same membrane as for Example 1a but here it was constituted by a stack of 8 elements, each with an effective surface area of 0.1 m². The total permeation surface area was thus 0.8 m². Under these conditions, the same oxygenated compound concentrations could be produced in the purified C4 cut as those obtained using the process of the invention in Example 1a.

The mixture for separation, SUPPLY, was identical to that of Example 1a. It was supplied in liquid form to pervaporation unit PV at a temperature of 50.0° C. Unit PV produced a liquid residue, RESIDUE, which was supplied to tray 6 of distillation column D, and a vapor phase permeate, PERMEATE, which was recovered after condensing.

The temperature of column D was between 115.4° C. at the bottom and 97.5° C. at the head.

Similarly to Example 1a, the vapor taken overhead from column D was partially condensed then decanted in separator B. The temperature measured in separator B was 88.9° C. A gaseous phase C3 was recovered from separator B. Since almost all of the water contained in the SUPPLY stream had been extracted in the PV unit and was therefore in the PERMEATE stream, no aqueous liquid phase was recovered in this case from separator B. Instead, an organic liquid phase was recovered and sent as a reflux to the head of distillation column D. The reflux ratio (ratio of the mass flow rate of the reflux liquid to the head of column D to that of the SUPPLY stream) in this instance was 0.57.

A purified C4 cut, PURIFIED C4, was obtained from the bottom of column D.

The material balance (flow rates and compositions by weight of the SUPPLY, C3, PURIFIED C4, PERMEATE and RESIDUE streams) from this process are shown in Table 1b.

TABLE 1b

Material balance in process of Example 1b.

| SUBSTANCE (WT %) | SUPPLY | C3 | PURIFIED C4 | PERMEATE | RESIDUE |
|---|---|---|---|---|---|
| C3 | 1.54 | 33.03 | 1.25 | 0.45 | 1.58 |
| C4 | 95.94 | 59.31 | 98.75 | 30.38 | 98.34 |
| Methanol | 2.44 | 4.87 | <1 ppm | 67.74 | 0.05 |
| Water | 0.05 | <1 ppm | <1 ppm | 1.42 | <1 ppm |
| Dimethyl-ether | 0.03 | 2.79 | 10 ppm | 0.01 | 0.03 |
| Flow rate $(g \cdot h^{-1} \cdot m^{-2})$ | 4000.0 | 40.0 | 3818.8 | 141.2 | 3858.8 |

Comparison of the results from Examples 1a and 1b illustrates the advantages of the invention. For the same mixture for treatment and the same purity of hydrocarbons obtained (same concentration of residual oxygenated compounds), and with the same type of membrane and identical pressure in the distillation zone as well as an identical number of distillation stages, the process offers:

a considerably reduced membrane surface area (0.2 m² instead of 0.8 m²);

greater purity of recovered methanol in the PERMEATE stream (89.27% by weight instead of 67.74% by weight) and in particular a lower water content (0.34% by weight instead of 1.42%) which facilitates its use in an etherification process;

reduced hydrocarbon loss in vapor C3 (21.3 g.h$^{-1}$ instead of 40.0 g.h$^{-1}$);

as a result of the two preceding points, a larger amount of recovered purified hydrocarbons (3868.4 g.h$^{-1}$ instead of 3818.8 g.h$^{-1}$).

Example 2

This Example illustrates the operation of the process of the invention when the mixture for separation is constituted solely by hydrocarbons and methanol, without water or dimethyl ether.

A stainless steel distillation column D with a diameter of 100 mm containing 60 perforated trays spaced by 5 cm was used, also a stainless steel pervaporation module provided with a membrane prepared using the method described in Example 2 of German patent DE-A-4 234 521. The module was constituted by an element with an effective permeation surface area of 0.1 m².

The mixture for separation (C4 cut) containing methanol, SUPPLY, was introduced via line 1 as a liquid at a temperature of 78.0° C. to plate number 12 of distillation column D, shown in FIG. 1. Column D was operated at an absolute pressure of 22 bar, measured in separator B. The column temperature was between 115.1° C. at the bottom and 73.7° C. at the head.

This time, the vapor taken overhead from column D via line 2 was completely condensed then returned via lines 6 and 7 as a liquid reflux to the head of column D. No vapor phase was removed from separator B, nor was any aqueous liquid phase removed via line 5. The temperature in separator B was 64.1° C. The reflux ratio (ratio of the mass flow rate of the reflux liquid to the head of column D to that of the SUPPLY stream) was 0.72.

A purified C4 cut, PURIFIED C4, containing less than 1 ppm by weight of residual methanol, was recovered from the bottom of column D.

A liquid phase, EXTRACTION, was extracted from tray number 8 of column D, at a temperature of 97.8° C., cooled to a temperature of 50.0° C. and supplied via line 10 to pervaporation unit PV. Unit PV produced a vapor phase permeate, PERMEATE, via line 13, which was collected after condensing, and a liquid residue, RESIDUE, which was returned to tray 18 of column D after reheating to 103.5° C.

The material balance (flow rates and compositions by weight of the SUPPLY, PURIFIED C4, EXTRACTION, PERMEATE and RESIDUE streams) from this process are shown in Table 2.

In this case too, the use of the process of the invention proved to be advantageous. The methanol concentration in the EXTRACTION stream (5.74% by weight) was substantially higher than that in the SUPPLY stream (2.44% by weight) but equal to that measured in separator B (3.68% by weight). Supplying pervaporation unit PV by a side EXTRACTION stream here too considerably reduced the required membrane surface area.

TABLE 2

Material balance from process of the invention in the absence of water and dimethyl ether

| SUB-STANCE (WT %) | SUPPLY | PURI-FIED C4 | EXTRAC-TION | PER-MEATE | RESI-DUE |
|---|---|---|---|---|---|
| C3 | 1.54 | 1.54 | 12.73 | 0.18 | 13.42 |
| C4 | 96.02 | 98.46 | 81.53 | 1.12 | 85.91 |
| Methanol | 2.44 | <1 ppm | 5.74 | 98.70 | 0.67 |
| Flow rate ($g \cdot h^{-1} \cdot m^{-2}$) | 4000.0 | 3901.0 | 1914.4 | 99.0 | 1815.4 |

Example 3

This example illustrates the operation of the process of the invention when oxygenated compounds are to be extracted from a C8 cut containing methanol and dimethyl ether.

A stainless steel distillation column D with a diameter of 100 mm containing 40 perforated trays spaced by 5 cm was used, also a stainless steel pervaporation module provided with a membrane which had been prepared using the method described in Example XVI of U.S. Pat. No. 5,152,898. The effective permeation surface area was 0.0125 m².

The mixture for separation, SUPPLY, was introduced as a liquid at a temperature of 120.0° C. into distillation column D via line 1, to tray number 10. Column D was operated at an absolute pressure of 3 bar, measured at separator B. The column temperature was between 182.2° C. at the bottom and 97.8° C. at the top.

The vapor taken overhead from column D via line 2 was partially condensed then decanted in separator B. The temperature in separator B was 64.8° C. Gaseous phase DME left separator B via line 4. The SUPPLY stream contained no water, so no aqueous liquid phase was recovered. The organic liquid phase obtained from line 6 was returned as reflux to the head of column D. The reflux ratio (ratio of the mass flow rate of the reflux liquid to the top of column D to that of the SUPPLY stream) was 0.56.

The majority of the purified cut C8, PURIFIED C8, was recovered as a liquid from the bottom of column D.

A liquid phase, EXTRACTION, was extracted from tray number 2 of column D at a temperature of 99.1° C., cooled to a temperature of 50° C. and supplied via line 10 to pervaporation unit PV. Unit PV produced a vapor phase permeate, PERMEATE, via line 13, which was collected after condensation, and a liquid residue, RESIDUE, which was returned to tray 14 of column D after reheating to 175.5° C.

The material balance (flow rates and compositions by weight of the SUPPLY, DME, PURIFIED C8, EXTRACTION, PERMEATE and RESIDUE streams) from this process are shown in Table 3.

TABLE 3

Material balance from process of the invention, Example 3

| SUB-STANCE (WT %) | SUP-PLY | DME | PURI-FIED C8 | EX-TRAC-TION C4 | PER-MEATE | RESI-DUE |
|---|---|---|---|---|---|---|
| C7 | 1.00 | 4.32 | 1.02 | 6.62 | 0.07 | 14.74 |
| C8 | 96.55 | 7.42 | 98.98 | 30.53 | 0.35 | 68.02 |
| Methanol | 2.42 | 21.79 | <1 ppm | 62.06 | 99.57 | 15.47 |
| Dimethyl-ether | 0.03 | 66.47 | <1 ppm | 0.79 | 0.01 | 1.77 |
| Flow rate ($g \cdot h^{-1} \cdot m^{-2}$) | 4000.0 | 1.8 | 3901.3 | 174.9 | 96.9 | 78.0 |

We claim:

1. A process for the separation of oxygenated compounds from a mixture of hydrocarbons of 3 to 8 carbon atoms containing the oxygenated compounds, comprising distilling the mixture in a distillation zone to produce overhead a gaseous distillate containing oxygenated compounds and hydrocarbons, at least partially condensing and at least partially recycling said gaseous distillate to the distillation zone, extracting a phase as a side stream from the distillation zone and sending said phase to a permeation zone comprising at least one membrane which is selectively permeable to alcohol; carrying out permeation on said phase, recovering at least one permeate enriched in alcohol downstream of the permeation zone, recovering a purified $C_{3-8}$-hydrocarbon mixture from the bottom of the distillation zone.

2. A process according to claim 1, wherein the pressure in the distillation zone is above 1 bar absolute, the head temperature is 40° C. to 120° C. and the bottom temperature is 70° C. to 200° C., and wherein the pressure in the permeation zone is greater than, equal to or less than the pressure in the distillation zone.

3. A process according to claim 1, wherein the residue is recycled to a tray where the composition is substantially the same as that of the residue.

4. A process according to claim 1, wherein the alcohol is methanol.

5. A process according to claim 1, wherein the permeate recovered is a vapor enriched in alcohol.

6. A process according to claim 1, wherein the oxygenated compounds consist of methanol and water, dimethyl ether or a mixture of water and dimethyl ether.

7. A process according to claim 1, wherein the phase extracted as a side stream consists of methanol, water, dimethyl ether and $C_{3-8}$ hydrocarbons.

8. A process according to claim 1, wherein the residue is recycled to the distillation zone.

9. A process according to claim 8, wherein the residue is recycled to a lower tray than that of the side stream extraction of said phase.

10. A process according to claim 1, wherein the phase is extracted as a side stream from at least one tray in the distillation zone where the alcohol concentration is at least equal to that of the alcohol in the hydrocarbon mixture.

11. A process according to claim 10, wherein the alcohol is methanol.

12. A process according to claim 11, wherein methanol is extracted from a tray in the distillation zone where the concentration of methanol is substantially maximal.

13. A process according to claim 1, wherein the oxygenated compounds comprise methanol and water, dimethyl ether or a mixture of water and dimethyl ether.

14. A process according to claim 13, wherein the purified hydrocarbon mixture from the bottom of the distillation zone has a water content of less than 10 ppm by weight, a dimethyl ether concentration of less than 100 ppm, and a methanol concentration of less than 50 ppm by weight.

15. A process according to claim 14, wherein the purified hydrocarbon mixture from the bottom of the distillation zone has a water content of less than 1 ppm by weight, a dimethyl ether concentration of less than 50 ppm by weight, and a methanol concentration of less than 5 ppm by weight.

16. A process according to claim 13, further comprising decanting and condensing the gaseous distillate, recovering and recycling to the distillation zone an organic liquid phase and optionally recovering an aqueous phase or a liquid or gaseous phase containing methanol and dimethyl ether.

17. A process according to claim 16, wherein the organic liquid phase is saturated with water.

18. A process according to claim 16, wherein the organic liquid phase is recycled to the head of a distillation column in the distillation zone with a reflux ratio of 0.3 to 3 times the mass flow rate of the hydrocarbon mixture.

19. In a process for the etherification of a hydrocarbon cut comprising olefin hydrocarbons containing 3 to 8 carbon atoms with methanol, in which said cut is reacted with the methanol in a reaction zone under etherification conditions, an effluent is recovered which contains organic ethers, hydrocarbons and oxygenated compounds, distillation is carried out to separate said ethers from said hydrocarbon mixture containing said oxygenated compounds, the improvement wherein the oxygenated compounds are separated from said hydrocarbon mixture according to the process described in claim 1, and at least a portion of methanol-enriched permeate obtained is recycled to the reaction zone.

20. A process according to claim 19 wherein distillation is carried out in a catalytic distillation zone and at least a portion of the permeate is optionally recycled to said catalytic distillation zone.

21. A process according to claim 19, wherein the effluent recovered from the reaction zone contains MTBE or TAME, and the oxygenated compounds comprise methanol and optionally water or dimethyl ether.

* * * * *